United States Patent [19]

Grubb et al.

[11] Patent Number: 5,037,957
[45] Date of Patent: Aug. 6, 1991

[54] CYSTEINE PROTEINASE INHIBITOR

[76] Inventors: Anders Grubb, Gilleskroken 5, S-222 47 Lund; Magnus Abrahamson, Dag Hammarskjölds väg 4B:108, S-233 64 Lund; Jerzy Trojnar, Stenöregatan 36, S-230 44 Vintrie, all of Sweden

[21] Appl. No.: 435,463
[22] PCT Filed: Jun. 17, 1988
[86] PCT No.: PCT/SE88/00334
§ 371 Date: Dec. 11, 1989
§ 102(e) Date: Dec. 11, 1989
[87] PCT Pub. No.: WO88/10266
PCT Pub. Date: Dec. 29, 1988

[30] Foreign Application Priority Data

Jun. 18, 1987 [SE] Sweden .................... 8702550

[51] Int. Cl.$^5$ .......... C07K 5/06; C07K 5/08; C07K 5/10; C07K 7/00
[52] U.S. Cl. .................... 530/330; 530/331; 564/152; 564/159
[58] Field of Search ............ 530/328, 329, 330, 331; 564/152, 159

[56] References Cited

U.S. PATENT DOCUMENTS 4,100,117 7/1978 Shields .................... 260/8

OTHER PUBLICATIONS

The Journal of Biological Chemistry, vol. 262, No. 20, Issued Jul. 15, 1987, pp. 9688–9694, "Identification of the Probable Inhibitory Reactive Sites of the Cysteine Proteinase Inhibitors Human Cystatin C and Chicken Cystatin".

Green et al., *J. Biol. Chem.* 1981, 256(4):1923–1928.

*Primary Examiner*—Lester L. Lee
*Assistant Examiner*—Stephen B. Maebius
*Attorney, Agent, or Firm*—Oblon, Spivak, McClelland, Maier & Neustadt

[57] ABSTRACT

New compounds which are cysteine proteinase inhibitors of the formula

B - A - C wherein
B = Pro-Arg-Leu-Val-Gly-, Arg-Leu-Val-Gly-, Leu-Val-Gly-, or Val-Gly-, or zero; the N-terminal amino acid optionally having a protective group,
A = a reactive group capable of specifically reacting with free-SH groups,
C = -Gly-Pro-Met-Asp-Ala; -Gly-Pro-Met-Asp; -Gly-Pro-Met; or -Gly-Pro, or zero;
with the proviso that B and C are not both zero.

5 Claims, No Drawings

CYSTEINE PROTEINASE INHIBITOR

The present invention relates to new compounds which are cysteine proteinase inhibitors interacting with the active sites of cysteine proteinases and, thus, inhibiting the degradation of peptides and proteins by cysteine proteinases.

Background

Cysteine proteinases are active in the intracellular protein and peptide catabolism of the body, in the extracellular degradation of collagen in the connective tissue of the body, and in the transformation of preproteins into their mature forms. If the activity of the cysteine proteinases is too high, different body tissues will be degraded at an excessive rate with consequent atrophy and impaired function. It is therefore of great importance that the activity of the cysteine proteinases of the body are accurately controlled. This is achieved, for example, in that the body fluids contain some ten proteins which inhibit cysteine proteinases. (Abrahamson M., Barrett A.J., Salvesen G., and Grubb A.: Isolation of six cysteine proteinase inhibitors from human urine. Their physicochemical and enzyme kinetic properties and concentrations in biological fluids. (1986) J. Biol. Chem. 261, 11282-11289).

Ischemic injuries, e.g. in connection with cardiac infarction, mean that body tissues are damaged by lack of oxygen. The extent of the final tissue damage increases since the cells primarily damaged by lack of oxygen release intracellular cysteine proteinases, which attack the surrounding normal tissue. The content of protein cysteine-proteinase inhibitors in the body fluids contributes to minimizing such secondary tissue damage which appears in connection with every ischemic injury.

Cysteine proteinases which are injected in different body fluids cause no damage as long as the inhibiting capacity of the protein cysteine-proteinase inhibitors of the body fluids is not exceeded. Proteinase overloading of the inhibitors entails very serious functional disorders, primarily hemorrhages. (Garvin P., Jennings R., Smith L., and Gesler R.: Chymopapain: A pharmacologic and toxicologic evaluation in experimental animals. (1965) Clin. Orthop. 41, 204-223). It may be mentioned that disc degeneration has been successfully treated with injections of cysteine proteinases in the damaged discs. When, unintentionally, the whole or part of the injection comes into the cerebrospinal fluid, severe cerebral hemorrhage is caused in the patients as a consequence of proteinase overloading of the total inhibiting capacity of the low content of protein cysteine-proteinase inhibitors in the cerebrospinal fluid. (Davies R., North R., Campbell J., and Suss R.: Multiple cerebral hemorrhages following chymopapain chemonucleolysis. (1984) J. Neurosurg. 61, 169-171). It has also been demonstrated that in connection with certain spontaneous cerebral hemorrhages, the patients exhibit a considerably reduced content of the protein cysteine-proteinase inhibitors in the cerebrospinal fluid. (Grubb A., Jensson O., Gudmundsson G., Arnason A., Lofberg H., and Malm J.: Abnormal metabolism of γ-trace alkaline microprotein. The basic defect in hereditary cerebral hemorrhage with amyloidosis. (1984) N. Engl. J. Med. 311, 1547-1549).

When the normal body tissue is penetrated by certain malignant cells and microorganisms, these malignant cells and microorganisms use cysteine proteinases to break down the resistance of the normal body tissue to such penetration. The protein inhibitors of cysteine proteinases in the body therefore are considered to play an important role for resisting such undesired tissue penetration. (Giraldi T., Sava G., Kopitar M., Brzin J., and Turk V.: Antimetastatic effects and tumour proteinase inhibition by spleen intracellular inhibitors of neutral proteinases. (1981) Eur. J. Cancer Clin. Oncol. 17, 1301-1306).

Many microorganisms, such as bacteria and viruses, produce their proteins as very large protein molecules which are then processed by proteolysis into the mature active smaller proteins used for the growth of the microorganisms and the invasion of the patient. If the initial protein stages cannot be broken down to the active proteins, the microorganisms will die, and it has been found that protein inhibitors of cysteine proteinases can stop viral attacks on cells. (Korant B., Brzin J., and Turk V.: Cystatin, a protein inhibitor of cysteine proteases alters viral protein cleavages in infected human cells. (1985) Biochem. Biophys. Res. Commun. 127, 1072-1076).

Prior art

Since a disturbed balance between the cysteine proteinases of the body and their inhibitors have been found to give rise to pathological changes, the research workers have tried to find ways to affect this balance by producing cysteine-proteinase inhibitors that could be supplied to the body. Two types of procedures have hitherto been used for providing such inhibitors in amounts that may be usable in clinical treatment.

One procedure resides in searching for natural cysteine-proteinase inhibitors in microorganisms. Such inhibitors have been found and isolated. Examples thereof are leupeptin and E-64. (Barret A., Kembhavi A., Brown M., Kirschke H., Knight G., Tamai M., and Hanada K.: L-trans-Epoxysuccinyl-leucylamido(4-guanidino)butane (E-64) and its analogues as inhibitors of cysteine proteinases including cathepsins B, H and L. (1982) Biochem. J. 201, 189-198). These substances have been demonstrated to positively affect atrophic diseases in experimental animals, but their structures differ from antigenic epitopes naturally present in man, and these substances may therefore, when injected, give rise to immunization with consequential immunologically produced side effects and reduced or suspended inhibitor effect.

The other procedure resides in determining the amino acid sequence immediately amino terminally of the peptide bond that is cleaved in a number of proteins which are known substrates for cysteine proteinases and synthesize small peptides whose sequence is identical with or closely resembles these sequences in the known substrates. To the carboxyl terminal portion of these peptides is further linked a reactive group reacting with the sulfhydryl group in the active centres of the cysteine proteinases and, thus, causing inhibition of these enzymes when bonding the substrate-like synthetic peptides. (Green G. and Shaw E.: Peptidyl diazomethyl ketones are specific inactivators of thiol proteinases. (1981) J. Biol. Chem. 256, 1923-1928). One problem encountered in connection with this procedure of producing cysteine proteinase inhibitors for use in human medicine is that the most important protein substrates of the cysteine proteinases in the body are not known. It is therefore difficult, or impossible, to theoretically predict which sequence or sequences of amino acids in the synthetic peptides might give rise to the most efficient and least toxic inhibitors. which are effective inhibitors of the body's own cysteine proteinases. The probably most important of these cysteine proteinase inhibitors is a protein called cystatin C (formerly called e.g. γ trace and post γ-globulin). Cystatin C has a single polypeptide chain comprising 120 amino acid residues and its amino acid sequence is known (Grubb A. and Löfberg H. (1982) Proc. Natl. Acad. Sci. USA, 79, 3024–3027). On the other hand, no one has hitherto identified any part of cystatin C constituting a substrate for cysteine proteinases and therefore, it has also been impossible to develop any peptide cysteine-proteinase inhibitors based on the structure of cystatin C.

Peptidyl diazomethyl ketones are potential inhibitors of cysteine proteinases since the diazomethyl group of the compounds can react with the cysteine side chain which is catalytically active in cysteine proteinases. Whether peptidyl diazomethyl ketones are effective inhibitors or not is determined by the peptide portion of the compounds. A good agreement between the peptide portion and the substrate pocket of the enzyme results in rapid and efficient inhibition on account of the "proximity effect". Previous assays of peptidyl diazomethyl ketones have shown that these ketones react irreversibly with cysteine proteinases, but not with assayed proteinases of the other three catalytic classes, i.e. serine-, aspartic acid- and metalloproteinases. (Green et al., ibid. and Barrett et al., ibid.). The peptide portion of the previously known peptidyl diazomethyl ketones has not been based on any portion of the structure of cystatin C.

Description of the invention

The present invention relates to new compounds which are cysteine proteinase inhibitors based on a segment of the peptide chain of cystatin C, namely amino acid residues 7-16 in cystatin C.

The compounds according to the invention can be administered in pharmaceutical preparations containing conventional constituents for therapeutic and/or prophylactic treatment of all such conditions where cysteine proteinase inhibition is desired.

In connection with this invention, it has been found that cystatin C contains a part of its peptide chain which constitutes a supersubstrate for cysteine proteinases, i.e. which extremely rapidly forms a very stable bond with the active centre of cysteine proteinases and in that connection, efficiently blocks these. In this process, these cysteine proteinases lose their ability to break down their natural substrates in the body. It has now been possible to identify the part of the polypeptide chain that constitutes its supersubstrate for human cysteine proteinases, and it has been demonstrated that peptides with homologous sequences either are rapidly cleaved by cysteine proteinases or, if the peptides are modified e.g. with groups reacting with sulfhydryl groups, efficiently inhibit the same cysteine proteinases. Since the modified peptides according to the invention originate from an evolutionary structure of the most effective inhibitor of cysteine proteinases in the human body, they are both efficient and probably devoid of side effects unrelated to their inhibition of the cysteine proteinases of the body.

The new compounds according to the invention, which are cysteine proteinase inhibitors, are of the formula

B - A - C wherein
B = Pro-Arg-Leu-Val-Gly-, Arg-Leu-Val-Gly-, Leu-Val-Gly-, or Val-Gly-, or zero; the N-terminal amino acid optionally having a protective group,
A = a reactive group capable of specifically reacting with free-SH groups,
C = -Gly-Pro-Met-Asp-Ala; -Gly-Pro-Met-Asp; -Gly-Pro-Met; or -Gly-Pro, or zero;
with the proviso that B and C are not both zero.

Suitable protective groups for the N-terminal amino acid in B are R-oxycarbonyl groups where R is a straight or branched alkyl having 3-18, e.g. 3-12, preferably 4-8 and most preferably 4 carbon atoms; aryl methyl where aryl is phenyl or naphthyl, e.g. benzyl; heteroamyl, e.g. piperidyl, pyridyl, picolyl or 9-fluorenyl methyl. Particularly preferred protective groups are t-butoxycarbonyl (Boc), benzyloxycarbonyl (Z), and acyl groups, such as acetyl.

Examples of A are diazomethylene, iodoacetic acid, chloromethyl, fluoromethyl and aminomethyl-diazomethyl ketone.

Synthesis of compounds according to the invention

The compounds according to the invention can be produced in a per se known manner by linking a protected amino acid to the following, optionally side chain protected amino acid to form a peptide bond between them and so forth, followed by the removal of the protective groups, as required, and finally reaction for inserting a reactive group.

Two compounds were synthesized in conventional manner according to the following reaction scheme where

| Boc | = t-butoxycarbonyl |
| Me | = methyl |
| Z | = benzyloxycarbonyl |
| Val | = valyl |
| Gly | = glycyl |
| Leu | = leucyl |

Boc-L-Val—OH + HCl.Gly—OMe

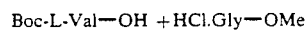

Boc-L-Val—Gly—OMe (1)

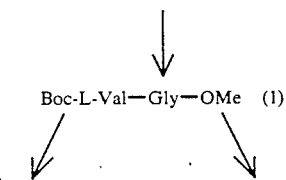

-continued

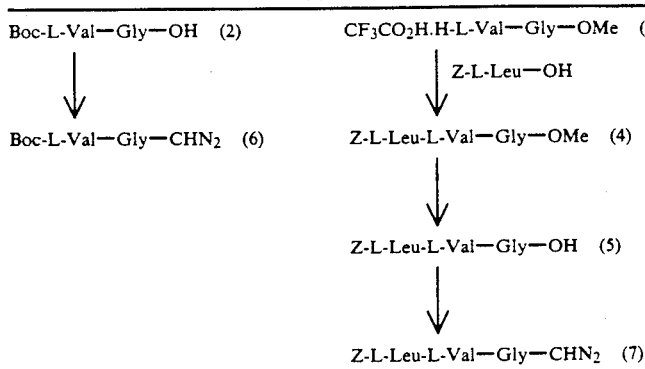

| Materials | From |
|---|---|
| 1. Boc-L-Val—OH | Bachem - USA (Cat. No. A-2455) |
| 2. Z-L-Leu—OH | Bachem - USA (Cat. No. C-2100) |
| 3. 1-Hydroxybenzotriazole | Janssen Chimica - Belgium |
| 4. N-methylmorpholine | Fluka AG - Switzerland |
| 5. Dicyclohexylcarbodiimide | Janssen Chimica - Belgium |
| 6. Trifluoroacetic acid | Janssen Chimica - Belgium |
| 7. Isobutyl chloroformate | Janssen Chimica - Belgium |

1. The synthesis of N-t-butyloxy-carbonyl-valyl-glycine methyl ester

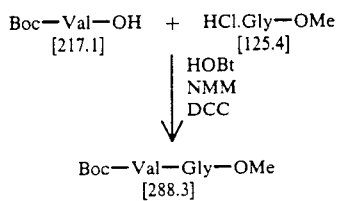

Glycine methyl ester hydrochloride (6.27 g, 50 mmol), 1-hydroxybenzotriazole (7.65 g, 50 mmol), t-butyloxy-carbonyl-L-valin (9.26 g, 50 mmol) and N-methyl-morpholine (5.75 g = 6.3 ml, 50 mmol) were dissolved in dry tetrahydrofurane (~30 ml). The solution was stirred and cooled in an ice-water bath while dicyclohexylcarbodiimide (10.8 g, 52.5 mmol) was added. Stirring was continued for 1 hour at 0° C. and an additional hour at room temperature. The N,N'-dicyclo-hexylurea which separated was removed by filtration, and the solvent was evaporated in vacuo. The residue was dissolved in AcOEt and washed with saturated $NaHCO_3$, water, 0.5M $KHSO_4$, water, saturated $NaHCO_3$, and water. The solution (AcOEt) was dried over $MgSO_4$ and evaporated in vacuo. The crystals were collected on a filter and washed with petroleum ether.

Yield: 9.73 g (67.5%): mp 111°-112° C.
TLC: ($C_6H_{12}$-AcOEt-MeOH 1:1:1): $R_f$=0.65
($CHCL_3$-MeOH-AcOH 10:2:1): $R_f$=0.87

2. The synthesis of N-t-butyloxycarbonyl-valyl-glycine

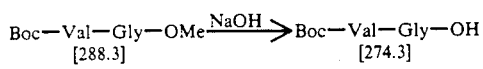

A solution of N-t-butyloxycarbonyl-L-valyl-glycine methyl ester (4 g, 13.8 mmol) in methanol (20 ml) was surrounded by a water bath of room temperature, and 1N NaOH (30.3 ml) was added with stirring. The mixture was left at room temperature for 2 hours. Diluted hydrochloric acid (13.8 ml, 1N HCl) was added, and methanol was removed in vacuo. The aqueous solution was cooled in an ice-water bath and stirred during acidification to pH 2-3 (about 16.5 ml 1N HCl). To the water with oil was added AcOEt. The water was extracted twice with AcOEt. The combined AcOEt layers were dried over anhydrous $MgSO_4$. The ethyl acetate was evaporated in vacuo. The residue was triturated with petroleum ether and the precipitate collected on a filter. The precipitate was dried in vacuo.

Yield: 3.27 g (86%); mp 58.5°-61° C.
TLC: ($CHCl_3$-MeOH-AcOH 10:2:1): $R_f$=0.64

3. The synthesis of L-valyl-glycine methyl ester trifluoroacetate

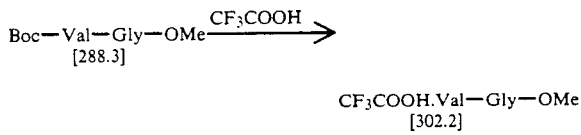

t-butyloxycarbonyl-L-valyl-glycine methyl ester (1.44 g, 5 mmol) was dissolved in trifluoroacetic acid (5 ml), and the mixture was left at room temperature for 1 hour. The solution was evaporated to dryness in vacuo and the residue triturated with dry ether.

Yield: oil (without purification to next step).

4. The synthesis of N-benzyloxycarbonyl-L-leucyl-L-valyl glycine methyl ester

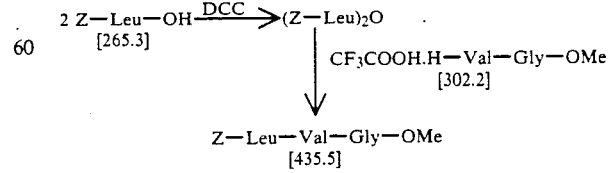

A solution of N-benzyloxycarbonyl-L-leucine (2.65 g, 10 mmol) in 15 ml $CH_2Cl_2$ was cooled in an ice-water bath and stirred with a magnetic stirrer. A solution of dicyclohexylcarbodiimide (2.58 g, 12.5 mmol) in CH₂Cl₂ was added, and stirring was continued for 15 minutes. Dicyclohexylurea was filtered. The solvent was evaporated in vacuo or at room temperature. The residue was dissolved in 4 ml DMF(1) and cooled in an ice-water bath. CF₃CO₂H·H-Val-Gly-OMe(1.51 g, 5 mmol) was dissolved in 7 ml DMF, and Et₃N (0.25 g =0.34 ml, 2.5 mmol) was added, whereupon the mixture was added to the solution (1) and Et₃N (0.34 ml) was again added. Stirring was continued for 24 hours at room temperature. The reaction mixture was filtered, diluted with water and AcOEt and separated. The water layer was extracted twice with AcOEt. Collected organic phases were washed once with water, once with 0.5M NaHCO₃, once with water, once with 1N HCl, and twice with water and dried over anhydrous MgSO₄. After filtration the solvent was evaporated in vacuo. The solid residue was triturated with petroleum ether, filtered and dried in vacuo.

Yield: 1.60 g (73.7%)
Amino acid analysis was correct.

5. The synthesis of N-benzyloxycarbonyl-L-leucyl-L-valyl-glycine

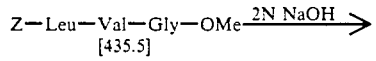

Z—Leu—Val—Gly—OMe $\xrightarrow{2N\ NaOH}$
[435.5]

Z—Ley—Val—Gly—OH
[421.5]

A solution of N-benzyloxycarbonyl-L-leucyl-L-valyl-glycine methyl ester (1.6 g, 3.67 mmol) in dioxan-methanol (1:1) (100 ml) was surrounded by a water bath at room temperature, and 2N NaOH (1.83 ml, 3.67 mmol) was added with stirring. The mixture was left at room temperature for 4 hours. The solvents were removed in vacuo. The residue was diluted with water and acidified with 2N HCl to pH 2. The solution was extracted five times with AcOEt. The organic layers were collected, dried over anhydrous MgSO₄ and evaporated to dryness in vacuo. The residue was dried in vacuo.

Yield: 4.45 g (87.6%): mp 185.5–187
TLC: (C₆G₁₂-AcOEt-MeOH 1:1:1): R$_f$=0.38

6. The synthesis of N-t-butyloxycarbonyl-valyl-glycine diazomethyl ketone

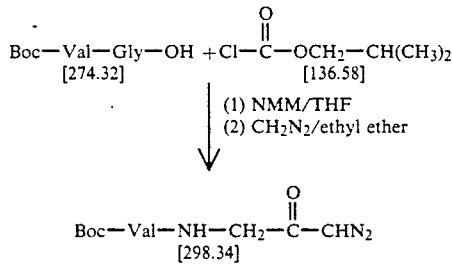

Boc-Val-Gly-OH (3.27 g=11.8 mmol) and N-methylmorpholine (1.19 g=1.3 ml =11.8 mmol) were dissolved in dry tetrahydrofuran (20 ml) and cooled to −20° C. under anhydrous conditions. Isobutyl chloroformate (1.61 g=1 53 ml=11.8 mmol) was added, and the mixture was stirred for 15 minutes at −20° C. Cold tetrahydrofuran (10 ml) was added, and the solution was filtered. The filtrate was added to a cold solution of diazomethane in ether (78 ml). The reaction mixture was kept at 0° C. and thereafter left at room temperature overnight. The solvent was removed under reduced pressure, and the product was crystallized from methanol-water.

Yield: 2.5 g (71.1%)
TLC: (CHCl₃-MeOH-AcOH 17:2:1): R$_f$=0.87

7. The synthesis of N-benzyloxycarbonyl-leucyl-valyl-glycine diazomethyl ketone

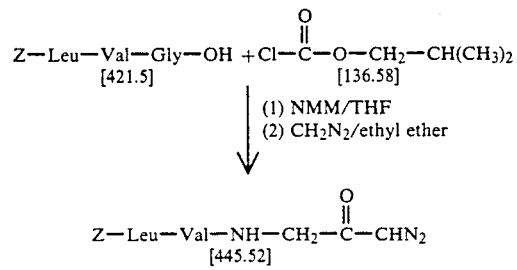

The title compound was synthesized by following the procedure stated under 6 above and by using the following reagents:

| | |
|---|---|
| Z—Leu—Val—Gly—OH | 4.45 g = 10.5 mmol |
| N-methylmorpholine | 1.06 g = 1.16 ml = 10.5 mmol |
| Isobutyl chloroformate | 1.43 g = 1.36 ml = 10.5 mmol |
| Diazomethane in ether | 70 ml |

Yield: 4 g (85.1%):R$_f$=0.87

Proteinase inhibiting properties of the compounds according to the invention Determination of rate constants for the interaction between the peptidyl diazomethyl ketones Z-Leu-Val-Gly-diazomethyl ketone (LVG) and Boc-Val-Gly-diazomethyl ketone (VG) and the cysteine proteinase model enzyme, viz. papain, is described below. Also, it was investigated whether LVG and VG inhibit the serine proteinase trypsin, a well-known example of proteinase acting with a catalytic mechanism different from that of cystein proteinases.

Materials

Papain (type III) from Sigma, trypsin (TPCK-treated) from Worthington; enzyme substrates Bz-DL-Arg-pNA and Z-Phe-Arg-NHMec from Bachem; and the peptidyl diazomethyl ketones according to the invention, synthesized as described above.

Enzyme activity measurements

Activity determination of papain was performed according to Barrett et al (ibid.), using Z-Phe-Arg-NHMec as substrate in 0.1M phosphate buffer, pH 6.5/1 mM DTT/1 mM EDTA at room temperature (22° C). All test dilutions were performed in 0.01% Brij 35. The reaction was started by substrate addition (20 μM final concentration) and stopped 10 minutes later by the addition of an equal volume of 0.1M NaCH₂Cl/NaAc, pH 4.3. Released fluorogen product was measured in a Perkin-Elmer MPF-43A spectrofluorimeter (excitation 360 nm, emission 460 nm) against a blank with the same contents as the test solution where chloroacetate had been added before the addition of enzyme/substrate.

Trypsin activity at pH 7.5 was measured at room temperature (22° C.) on samples in buffer with a final concentration of 25 mN Tris/25 mM CaCl₂ The reaction was started by the addition of Bz-DL-Arg-pNA to 2.5 mN final concentration and stopped after 10 minutes by the addition of an equal volume of 50% (v/v) HAc. Released paranitroaniline was meausred spectrophotometrically (Perkin-Elmer 550S) at 405 nm. Absorbancy values for blank (HAc addition before enzyme/substrate addition) were subtracted before evaluation.

Determination of rate constants for inactivation of papain

The molar active concentration of the papain solution used was determined by titration with E-64 (Barrett et al., ibid.). Stock solutions (1 mM) of LVG and VG were prepared by weighing 10 $\mu$mol of the respective peptidyl diazomethyl ketone which was thereafter dissolved in 500 $\mu$l acetonitrile (LVG) or 100 $\mu$l DMSO (VG), whereupon the volumes were adjusted to 10 ml with water. The exact concentration of peptidyl diazomethyl ketone was experimentally established, such that the reaction proceeded within a reasonable time with regard to the measuring technique used. Enzyme ($2 \times 10^{-8}$ M final concentration) and peptidyl diazomethyl ketone were mixed at zero time. 25 $\mu$l samples were withdrawn at suitable times (15 s–10 min.) and therafter immediately added to mixtures for enzyme activity determination (see above). The dilution then obtained efficiently stopped continued reaction between enzyme and peptidyl diazomethyl ketone.

Evaluation of experimental data was made in the manner described by Barret et al. (ibid.), where
i=concentration of inhibitor (here peptidyl diazomethyl ketone)
e=concentration of enzyme (here papain)
Enzyme activation can be schematically described as

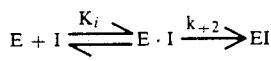

$$E + I \underset{}{\overset{K_i}{\rightleftharpoons}} E \cdot I \overset{k_{+2}}{\longrightarrow} EI$$

When i>>e, the following equation applies to the kinetics of inactivation:

$$\ln \frac{a_t}{a_o} = -k_{+2}t/(1 + K_i i)$$

where $a_o$ is enzyme activity (here measured as amount of released fluorogen product from the substrate Z-Phe-Arg-NHMec) at zero time, and $a_t$ is enzyme activity at time t.

When semilogarithmic plots of $a_t$ against t were found to be linear, the rate constant for the observed inactivation (pseudo-first-order reaction), $k_{obs}$, was calculated as ln 2/$t_{0.5}$. The apparent rate constant $k'_{+2}$ (second order) for the inactivation in the scheme

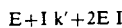

$$E + I \: k'_{+2} E I$$

was caculated as $k_{obs}/i$.

Papain was incubated with LVG and VG in a 12-fold molar excess, and samples were withdrawn at different times for determining residual enzyme activity. From experimental data, the apparent rate constants ($k'_{+2}$) were calculated for LVG as $3 \times 10^5 M^{-1}s^{-1}$ and for VG as $5 \times 10^3 M^{-1}s^{-1}$. Blanks consisting of solvents for the compounds showed no inhibition of the papain activity.

Incubation of the serine proteinase trypsin with LVG and VG in 250-fold molar excess gave no inhibition of the enzyme acitivity, even after incubation for one hour.

As a comparison it may be mentioned that tests with a synthetic peptide corresponding to position 4-21 in cystatin C (synthesized on request by Ferring AB, Malmö, Sweden) show that this peptide does not at all inhibit papain, but, in contrast, is an excellent substrate for this enzyme and is then cleaved at the glycine-glycine-peptide bond corresponding to the proposed inhibition centre in cystatin C.

The results from the tests now described show that LVG and VG are efficient inhibitors of the cysteine proteinase papain, but do not exhibit any inhibitory activity against the serine proteinase trypsin. The tripeptidyl compound LVG was found to be about 100 times more effective than the dipeptidyl compound VG as papain inhibitor, which confirms the assumption that an extension of the peptide portion of the tested peptidyl diazomethyl ketones according to the invention by one or more amino acids fitting into the substrate pocket of the enzyme enhances the inhibitory effect because of increased bonding energy. Since LVG and VG are synthesized after the amino acid sequence which is positioned immediately N-terminally of the reactive site bond now shown of the native proteincysteine proteinase inhibitor cystatin C, and papain has a substrate pocket holding seven amino acid residues, four of which are positioned N-terminally of the hydrolyzed substrate bond (Schechter I., Berger A., On the size of the active site in proteinases. I Papain, Biochem. Biophys. Res. Commun. 1967:27, 157–62), it is likely that an extension of the peptide portion of the peptidyl diazomethyl ketone in accordance with the sequence of cystatin C yields an inhibitor having still more effective inhibitory properties.

The apparent rate constant for VG inhibition of papain is of the same order of magnitude as the rate constants for other, previously reported dipeptidyl diazomethyl ketones (Green et al., ibid.; Barrett et al., ibid.) while the rate constant for LVG inhibition of papain is of the same order of magnitude as the constant for the highly effective epoxide-cysteine proteinase inhibitor E-64 (Barrett et al., ibid.). As opposed to the microbial inhibitor E-64, cysteine proteinase inhibitors according to the invention, which have been synthesized on the basis of the inhibitory reactive site sequence of cystatin C, offer, in addition to the same effective inhibition degree, the further advantage of having specificity to individual cysteine proteinases coinciding with the endogenous inhibitor cystatin C of mammals.

Inhibition by LVG of other types of cysteine proteinases in addition to those of the papain type Since LVG has been synthesized in accordance with the structure of the supersubstrate portion (inhibition centre) of cystatin C, it could be expected that LVG would inhibit the same type of cysteine proteinases as cystatin C, i.e. cystein proteinases of the papain type. Surprisingly, it was however found that LVG in addition effectively inhibits other types of cystein proteinases, e.g. human calpain and streptococcal proteinase. Also, LVG was found to inhibit the growth of group-A streptococci which all produce streptococcal proteinase.

Materials

Streptococcal proteinase was purified from group-A streptococci as earlier described (Liu T.-Y, Neumann N., Elliott S., Moore S., Stein W. (1963) J. Biol. Chem. 238, 251–256).

Calpain was purified from fresh human red blood corpuscles as earlier described (Kuboki M., Ishii H., Kazama M., Procalpain is activated on the plasma membrane and the calpain acts on the membrane (1987) Biochim. Biophys. Acta 929, 164–172).

Inhibition of the enzyme activity of streptococcal proteinase with LVG

The isolated streptococcal proteinase (15 mg/ml) was diluted to 0.0625 mg/ml with 0.4M phosphate buffer, pH 6.5/4 mM EDTA/4 mM DTT and then activated by incubation at 37° C. for two hours. To a constant volume of the active streptococcal proteinase was thereafter added a constant volume of LVG solutions with increasing LVG concentration. After incubation for 5 min. at 37° C., the substrate azocasein was added and after additional incubation for exactly 15 min. at 37° C., the reaction was stopped by the addition of 20% TCA (trichloroacetic acid). The samples were centrifuged and the absorbancy of the supernatant was read at 366 nm. It was found that 10 μM LVG concentration was sufficient to give a total inhibition of the proteinase activity in the streptococcal proteinase solution (containing 0.0625 mg/ml of the proteinase).

Inhibition of group-A streptococcal growth with LVG

Group-A streptococci were cultured on blood agar discs as in routine diagnosis for determining sensitivity to antibiotics. The discs applied on the culture gel and used for supplying different types of known antibiotics were this time soaked instead with 20 μl of a solution having an LVG concentration of 1 mM. All tested isolates of group-A streptococci and all tested reference strains of group-A streptococci were effectively inhibited in growth by the LVG solutions. When the growth of group-A streptococci was tested in free solution, a MIC value for LVG concerning group-A streptococci could be determined at about 1 μg/l. (MIC=minimal inhibiting concentration). If a molar excess of isolated streptococcal proteinase was added to the solution of LVG before this was applied to the bacterial cultures, there was obtained no effect on the bacterial growth, which indicates that the antibacterial effect of LVG is mediated by its cysteine proteinase inhibiting ability.

Ten mice were injected intraperitoneally with lethal doses of group-A streptococci. Five of them received after a period of 45 min. 0.2 mg LVG in 0.5 ml 1% dimethyl sulfoxide in physiological sterile saline by a second intraperitoneal injection. The remaining five mice obtained an identical second injection except that it did not contain any LVG. After one day only the five mice injected with LVG were still alive.

These experiments show that compounds according to the invention can cure diseases caused by microorganisms using cysteine protenases for multiplication and/or tissue penetration. Examples of such microorganisms are: group-A streptococci, Entamoeba histolytica, rhino virus and polio virus and other Picorna viruses

Inhibition of the enzyme activity of human calpain with LVG

Isolated human calpain (0.15 mg/ml) in 20 mM Tris buffer, pH 7.5/5 mM CaCl$_2$/6 mM dithiothreitol was supplied with a substrate (0.4% casein in 0.1 M imidazole buffer, pH 7.5/5 mM CaCl$_2$/6 mM dithiothreitol) and different amounts of LVG. After incubation for 30 min. at 37° C., the reaction was stopped by the addition of trichloroacetic acid to a final concentration of 2.5%, and the samples were centrifuged, whereupon the absorption of the supernatant at 280 nm was measured. It was found that complete inhibition of the calpain (2.5 μg/ml) was obtained at a final concentration of LVG of 1 μM.

We claim:

1. Compound of the formula

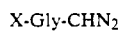

X-Gly-CHN$_2$ wherein X is selected from the group consisting of
Pro-Arg-Leu-Val-,
Arg-Leu-Val-,
Leu-Val-,
Val-,
and protected derivatives thereof, wherein the N-terminal amino acid has a protective group.

2. Compound as claimed in claim 1, wherein said compound has the formula: protective group-Leu-Val-Gly-CHN$_2$.

3. Compound as claimed in claim 1, wherein said compound has the formula: protective group-Val-Gly-CHN$_2$.

4. Compound as claimed in claim 1, wherein said compound is N-t-butyloxycarbonyl-valyl-glycine-diazomethyl ketone.

5. Compound as claimed in claim 1, wherein said compound is N-benzyloxycarbonyl-leucyl-valyl-glycine-diazomethyl ketone.

* * * * *